United States Patent [19]
Shaik

[11] Patent Number: 5,944,988
[45] Date of Patent: Aug. 31, 1999

[54] CHROMATOGRAPHY BUFFERS CENTER

[75] Inventor: Gaffar Abdul Shaik, Northridge, Calif.

[73] Assignee: Shaik A. Gaffar

[21] Appl. No.: 09/053,311

[22] Filed: Apr. 1, 1998

[51] Int. Cl.⁶ .................................................... B01D 15/08
[52] U.S. Cl. ....................... 210/198.2; 210/656; 210/101; 210/541
[58] Field of Search .................................... 210/656, 101, 210/198.2, 541; 422/70, 100, 102, 103

[56] References Cited

U.S. PATENT DOCUMENTS

| | | | |
|---|---|---|---|
| 4,064,737 | 12/1977 | Sieverin | 422/103 |
| 4,418,040 | 11/1983 | Karamian | 422/101 |
| 4,889,692 | 12/1989 | Holtzman | 422/102 |
| 5,265,642 | 11/1993 | Buckminster | 210/198.2 |
| 5,275,723 | 1/1994 | Greenley | 210/198.2 |
| 5,407,569 | 4/1995 | Greenley | 210/198.2 |

*Primary Examiner*—Ernest G. Therkorn

[57] ABSTRACT

The described Chromatography Buffers Center holds various types of buffers required in the purification of a variety of biological molecules. The unit consists of a base plate, a handle, reservoirs and lids with attached stop pins. The vertical handle, which is an extension of base plate, gives a nonslippery grip to lift and carry the unit. A short bent hook present in the handle is useful to mount the unit in a clamp that is attached to a common laboratory stand. The hook permits lateral movement of the unit even by a simple push with a finger. Base plate allows the unit sit on any flat surface of work bench, shelf or magnetic stirrer. Reservoirs attached permanently to the top of base plate hold different types of buffers in their chambers. Through drain tubes present in the rim of base plate, these buffers can be drawn to develop chromatography columns. Lid on each reservoir protects buffer from air born dust and evaporation. Each lid on its bottom edge, has a groove that allows it to sit firmly on the rim of reservoir. Several other short but deep grooves not only provide ventilation but also drain buffer and other liquids rapidly, when needed. Lid also carries a permanently fixed stop pin. By attaching the end of tubing to stop pin, the flow of buffer can be stopped, instantly. More fresh buffer can be added to reservoirs easily at any time by simply removing the lid.

19 Claims, 12 Drawing Sheets

CHROMATOGRAPHY BUFFERS CENTER

BACKGROUND OF THE INVENTION

This invention specifically relates to chromatography used in biochemical and immunochemical studies.

Chromatography is a technique employed for isolating a biological molecule from a mixture containing possibly hundreds of other contaminating molecules. Isolation of an enzyme from crude cell-free extract is an example. The general requirements for chromatography are a solid phase consisting a matrix with a functional group and a liquid phase containing a buffer for washing and elution. These two phases play intricate role in the success of experiments. Since biological molecules vary from one another in size, shape, charge, composition and function, different types of chromatography procedures are developed based on distinct strategies. For instance, sieving chromatography separates molecules based on size, and ion-exchange chromatography isolates biologicals based on +ve or −ve charge. Affinity chromatography, on the other hand, purifies a molecule based on its specific function. At present, affinity chromatography with variations is used in purifying a variety of proteins such as receptors, enzymes, antigens, antibodies and several types of recombinant proteins produced by genetic engineering.

However, chromatography requires several buffers. The number and variety of buffers needed in a procedure depends upon the type of components involved and the nature of their interaction. In sieving chromatography, a single buffer is used to eluate proteins from the column. In ion-exchange chromatography, where there is interaction between +ve and −ve charges, a minimum of 2 to 4 types of buffers are required. But, in affinity chromatography, where specific function of a molecule is involved, the variety and number of buffers needed vary considerably. In a typical procedure, an affinity column needs wash buffer, binding buffer, pre-elution buffer, elution buffer, stripping buffer, and storage buffer. The composition, pH and ionic strength of the above mentioned buffers differ considerably from one another. Since their purposes are different, these buffers should not be mixed or contaminated one with the other. Chromatography Buffers Center is ideally suited to hold and supply these differing buffers during the purification of biological molecules.

Technical problems associated particularly with the liquid phase of chromatography and the solutions offered by Chromatography Buffers Center are best explained by taking affinity chromatography as an example. The preferred method of doing this chromatography is by packing affinity beads in a column. Protein solution and various buffers are then passed through. When the volume of protein solution is small, different buffers are added in small aliquots by using a pipette. As the added solution percolates into the beads, more is added. In this approach, every time a buffer is added, the top part of gel bed gets disturbed sending beads floating in the buffer. The floating beads then nonspecifically stick to the wall of column. More the height of added buffer, greater the amount of adsorption of beads to the surface. The adsorbed beads can not be processed since they are not in gel bed. This type of loss of beads results in decreased protein binding capacity of the column. The column adsorbed beads may even contaminate the purified end product by untimely releasing other molecules. This is the first problem.

The volume of added buffer and the amount present on gel bed can be kept low to minimize the loss of beads during the run. However, any delay between additions of buffer makes gel bed go dry, crack and then trap air. A column once dried initiates unpredicted behaviour in the elution pattern of proteins. The end result is getting only a partially pure protein, low yield and highly diluted solution. This is the second problem.

In affinity chromatography, different types of buffers are taken usually in containers such as beakers or flasks. Any mistake in the sequence of addition of buffers from these congregated containers, results in getting less than desired end product. Even, total or partial loss of protein is not uncommon. Because of divided attention between collecting buffer and not allowing gel bed go dry, adding wrong buffer at right time is common. This is the third problem.

Another method of adding buffers to affinity column is by using a peristaltic pump containing a tubing. Keeping the end of tubing always submerged in buffers is very important. The tube is generally attached to the wall of buffer container such as a beaker by an adhesive tape. Because the surface is moist, adhesive tape does not stick strongly and often releases the tubing. The tubing which usually comes as coil, tends to go into coil. This makes the tubing end come out of buffer. If not paid immediate attention, air is pumped into the column which makes the gel bed go dry and crack. This is the fourth problem.

Also, to pump different buffers, the tubing has to be transferred from one buffer container to another. This makes buffers get contaminated either with proteins or with other buffers. When several chromatography runs have to be made, contaminated buffers can cause serious problem in the isolation of a pure protein. This is the fifth problem.

A different approach to adding buffers is by using special equipment. These instruments pump buffers steadily and also switch valves automatically to pump one buffer after another as dictated by a computer. The drawbacks with these instruments, besides prohibitive cost, are leaky valves, need of extra time to warm up and necessity for a lot of buffer for washing and priming pumps and system lines. Maintaining these instruments is costly and time consuming. Some of the affinity chromatography buffers are expensive to waste for washing and priming pumps. Even though, these instruments still need separate containers to hold different types of buffers. In these containers, tubing end surfacing in buffers is a real problem. Therefore, for many laboratories which have limited budget and need, these expensive instruments are least desired. Such labs need alternate instruments. This is the sixth problem.

In brief, keeping gel surface flat with minimum amount of buffer on the top of gel bed, never allowing column go dry, letting the tubing end stay in solution, eliminating cross-contamination of buffers and feeding columns at a steady flow, play important role in obtaining a pure protein.

OBJECTS AND ADVANTAGES

The objects and advantages of the Chromatography Buffers Center are:

1. To provide several reservoirs on a single base plate so that different types of buffers can be placed in an order at one level.
2. To provide drain tubes in the base plate so that buffers can be drawn till the last drop from the bottom of reservoirs.
3. To position drain tubes cryptic so that unit can be handled with no injuries to persons and no damages to property.
4. To provide an extra drain tube to one of the reservoirs so that a gradient buffer can be prepared in the same unit.

5. To provide stop pin in the lid of reservoir so that tubing can be attached for stopping the flow of buffer, instantly.
6. To fabricate base plate and handle from one piece of material so that there is no need for using nuts and bolts.
7. To make handle with a broad top for a nonslippery grip.
8. To provide enough gap between reservoirs and handle so that there is enough room for a hand to grip.
9. To install a hook in the handle so that unit can be easily mounted in a clamp attached to a vertical stand.
10. To fabricate a hook that saves space, causes no obstruction, rotates easily side to side and helps in removing the unit from clamp without manipulating any additional nuts and bolts.
11. To fabricate a special clamp for accepting the hook attached to Chromatography Buffers Center.
12. To calibrate reservoir wall for indicating buffer volume.
13. To provide transparency so that status of buffer can be viewed clearly; and
14. To fabricate the unit and its accessories from commonly available materials which are durable, hard and tough to break.

Further objects and advantages will be apparent from the following description and drawings.

BRIEF SUMMARY OF THE INVENTION

Chromatography Buffers Center holds different kinds of buffers required in the purification of a variety of biological molecules. It has a sturdy handle to lift and carry the unit with a firm grip. Hook in the handle can be used to mount the unit in a clamp attached to a stand. The hook also permits lateral movement of the unit in clamp by a simple push with finger. Base plate allows the unit sit on any flat surface such as that of work bench, shelf or magnetic stirrer. Buffer reservoirs are attached to the top of base plate, permanently. These buffers flow out from reservoirs through drain tubes present in the base plate. Each lid has special groves in the rim which make the lid sit firmly on the top of reservoir, provide ventilation and also quickly drain buffer or other liquids. Lid also protects buffer from surface evaporation and air born dust, The unit operates by gravity. It can also work in conjunction with peristaltic pump and instruments having valve regulator. The unit is simple to use and easy to maintain.

BRIEF DESCRIPTION OF THE DRAWINGS

In the drawings, all closely related figures have same number but different alphabetic suffixes.

REFERENCE NUMERALS IN DRAWINGS

| | |
|---|---|
| 20 | "L" shaped plate |
| 22 | Base plate |
| 24 | Vertical handle |
| 26 | Front end of base plate |
| 28 | Drain tubes (A, B, C, D, E) |
| 30 | Reservoirs |
| 32 | Hole of base plate |
| 34 | Handle top |
| 36 | Hole in handle top |
| 38 | Hook |
| 40 | Graduation mark |
| 42 | Lid |
| 44 | Stop pin |
| 46 | Groove in lid |
| 48 | Deep groove in lid |
| 50 | Short arm |
| 52 | Long arm |
| 54 | Hex nut |
| 56 | Cap nut |
| 58 | Clamp |
| 60 | Hole in clamp |
| 62 | Groove in clamp |
| 64 | Side of clamp groove |
| 66 | Thumb screw |
| 68 | Tubing |
| 70 | Buffer distributor |
| 71 | Connecting tubes (M, N, 0, P, Q) |
| 72 | Stop-cock |
| 74 | Chromatography column |
| 76 | Peristaltic pump |
| 78 | Valve regulator |

DETAILED DESCRIPTION OF THE INVENTION

Figure 1:
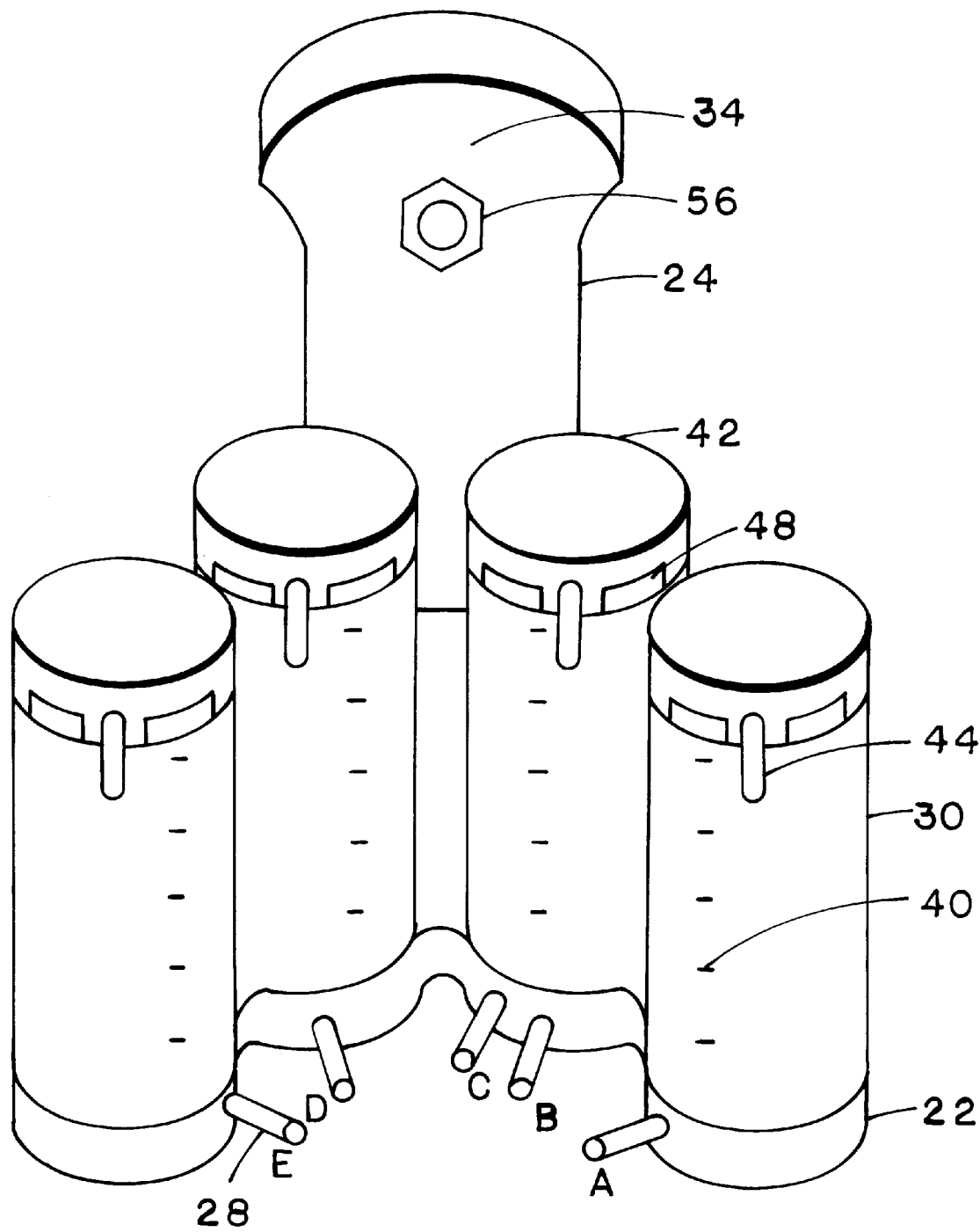
FIG. 1 shows a perspective view of Chromatography Buffers Center with four reservoirs.
Figure 2:
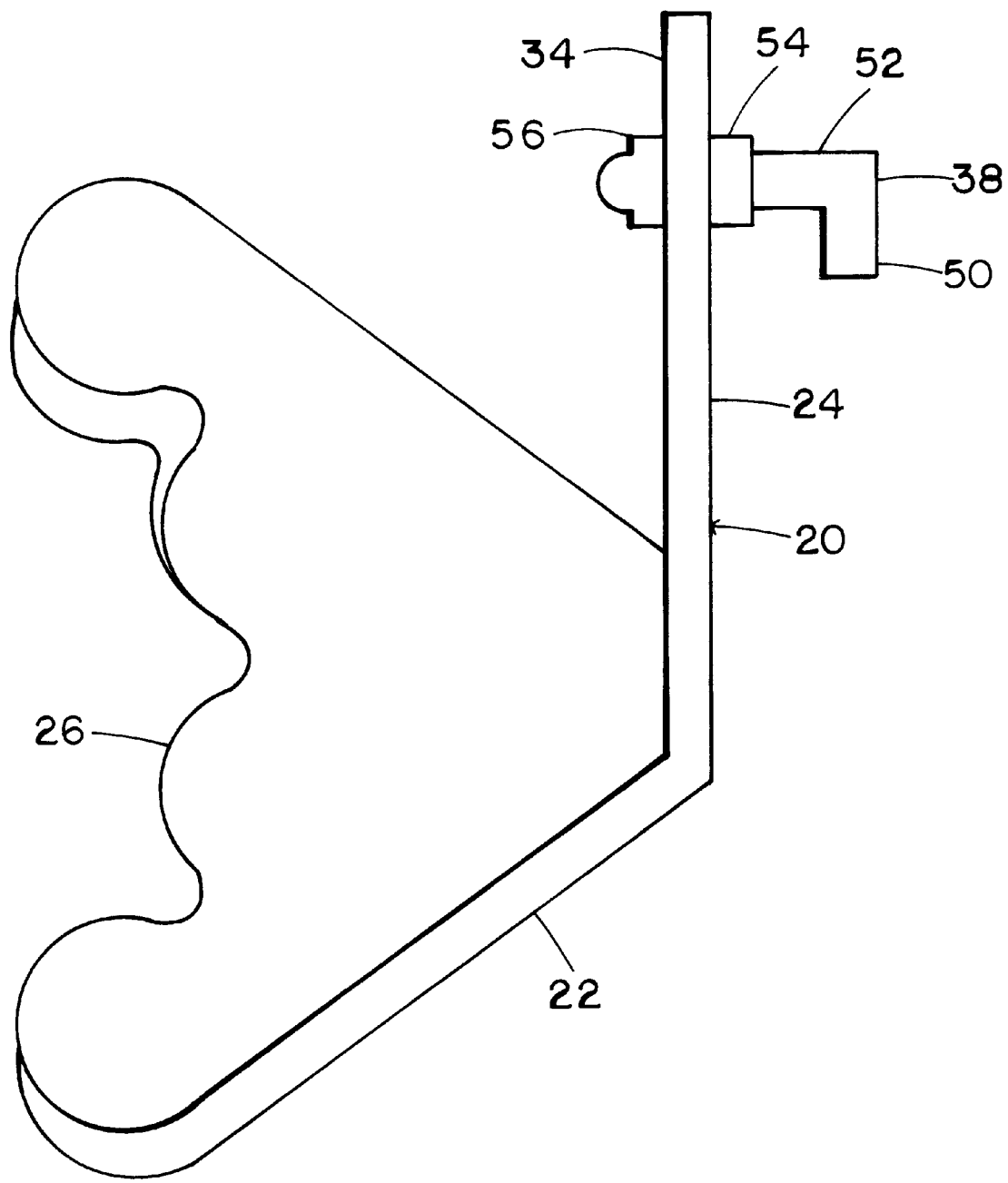
FIG. 2 shows a side view of base plate and handle with hook.

A perspective view of the first preferred embodiment of Chromatography Buffers Center is shown in FIG. 1. This unit has an "L" shaped plate 20 of uniform thickness (FIGS. 1,2). A single continuous piece of acrylic having length between 10" and 15", width between 8" and 12" and thickness between 0.3" and 0.5" is cut, shaped by machining and then bent in the middle of its length by applying heat. This results in a flat base plate 22 and a vertical handle 24 without any need for nuts and bolts. Slightly thick or thin, clear or colored acrylic can also be used for this purpose.

The front end 26 of base plate is made broad to accommodate buffer reservoirs (FIG. 2). The base plate carries drain tubes 28 (A, B, C, D, E), made of brass, in its rim and reservoirs 30 on its top. To fit drain tube, a hole of about 1" long is drilled in the middle of the rim perpendicular to the surface of the base plate below each reservoir. A suitably long piece of tube is then inserted and fixed permanently, using epoxy based glue. Each drain tube is made to communicate with another short vertical hole 32 drilled in the top of base plate (FIG. 3) so that drain tube opens into the reservoir chamber. The size and number of drain tubes and their corresponding holes can be varied depending upon need.

Figure 3:
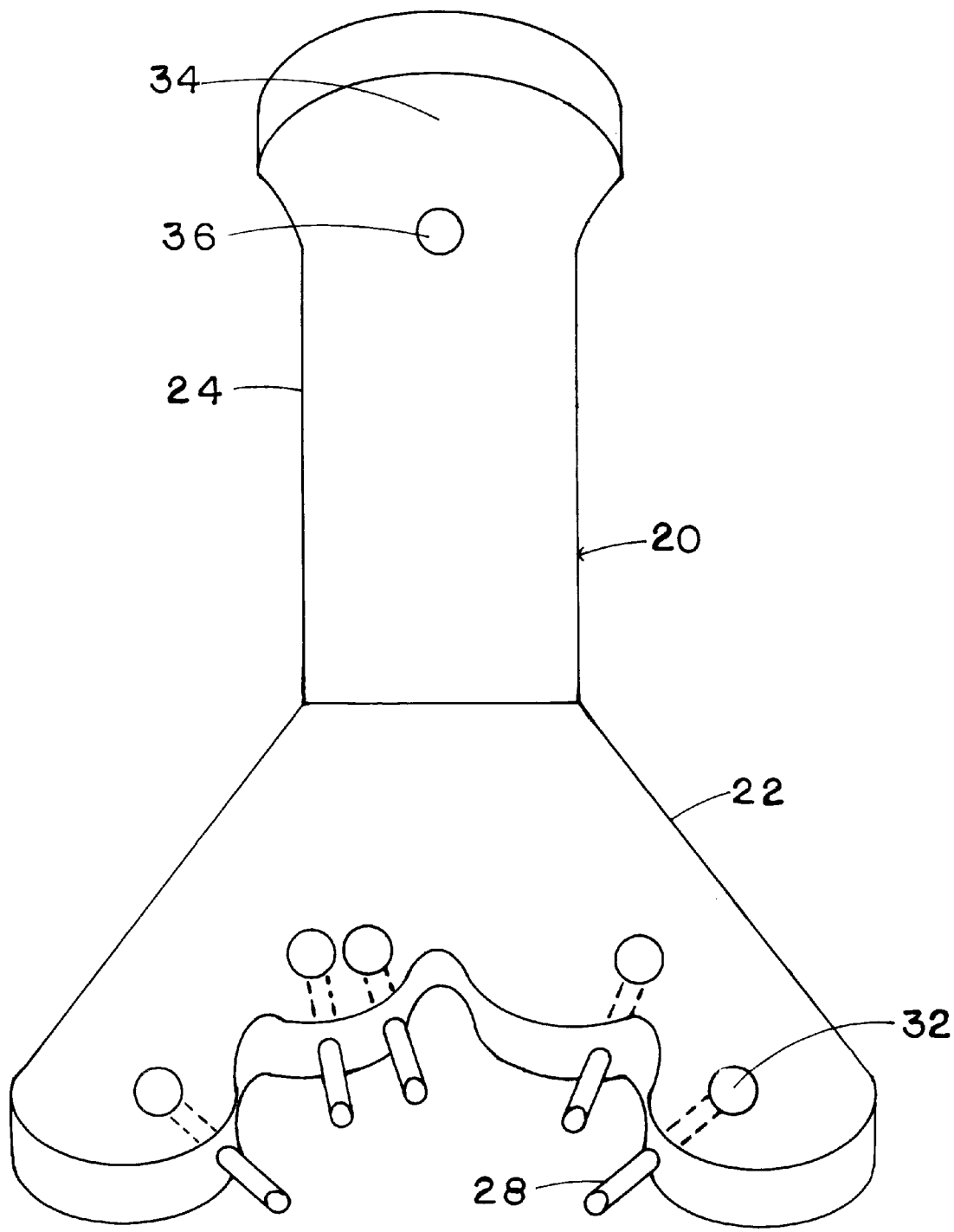
FIG. 3 shows holes in the top surface of base plate.

The vertical handle 24, which from its top to bottom has at least 1" gap from the nearest reservoirs, remains as a sturdy integral part of the unit (FIGS. 1, 2). The handle top 34 is made wide for a nonslippery grip (FIGS. 1, 3). The handle top has a hole 36, which cuts across both flat surfaces, ranges in diameter from 0.3" to 0.5" (FIG. 3). This hole accepts a hook 38 (FIG. 2).

Figure 7:
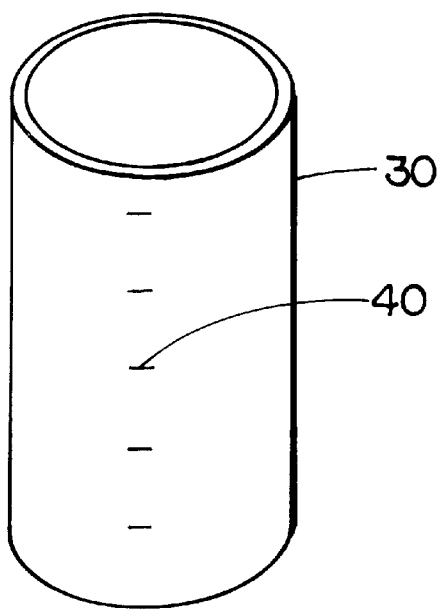
FIG. 7 shows a reservoir with graduation marks.

Each buffer reservoir 30, a clear transparent tube, has length between 4" and 6", outer diameter between 1.5" and 3" and wall thickness between 0.1" and 0.4" (FIGS. 1, 7). One end of each reservoir is permanently attached in a specified location on the top of base plate using solvent adhesive. The outer surface of reservoir is etched with graduation marks 40 to indicate approximate volume (FIGS. 1, 7). Each reservoir, immediately below its location, contains one drain tube in the base plate. However, the second reservoir from left contains two drain tubes 28B, 28C (FIGS. 1, 3).

Figure 8A:
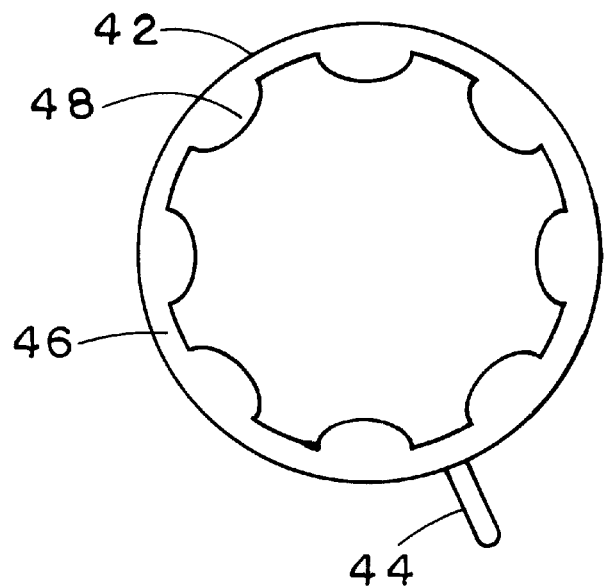
FIG. 8A shows bottom view of lid with grooves and stop pin.
Figure 8B:
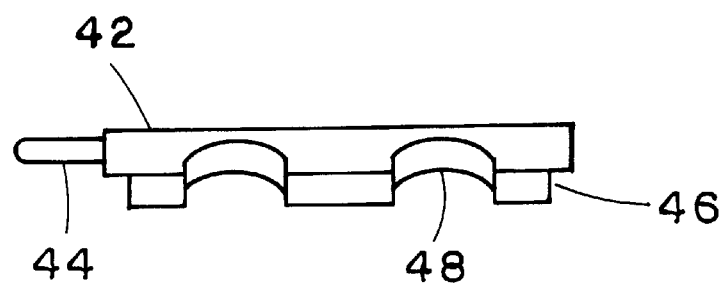
FIG. 8B shows side view of lid with grooves and stop pin.

Each lid 42 having an outer diameter ranging between 1.5" and 3", and thickness between 0.3" and 0.5", sits on the top of buffer reservoir (FIGS. 1, 8). The lid has stop pin 44, made of brass, in its rim (FIGS. 1, 8). Each stop pin is attached permanently to lid first by drilling a suitable hole in the middle of its rim, perpendicular to surface and then using epoxy based adhesive to hold the pin in place. The lid in its flat bottom has a groove 46 cut along its edge (FIG. 8A) to accommodate the rim of reservoir. Additional equally spaced grooves 48 are also cut in the edge. These are approximately 0.3" to 0.5" deeper and slightly taller than the groove for the rim of reservoir (FIGS. 1, 8). However, these grooves do not cut the top surface of lid. When lid sits on the reservoir, the deep grooves open the chamber of reservoir to out side.

Figure 11:
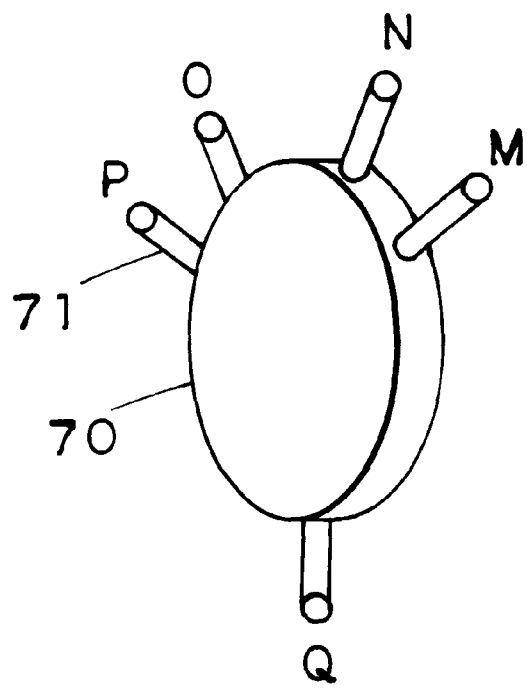
FIG. 11 shows details of buffer distributor.
Figure 12:
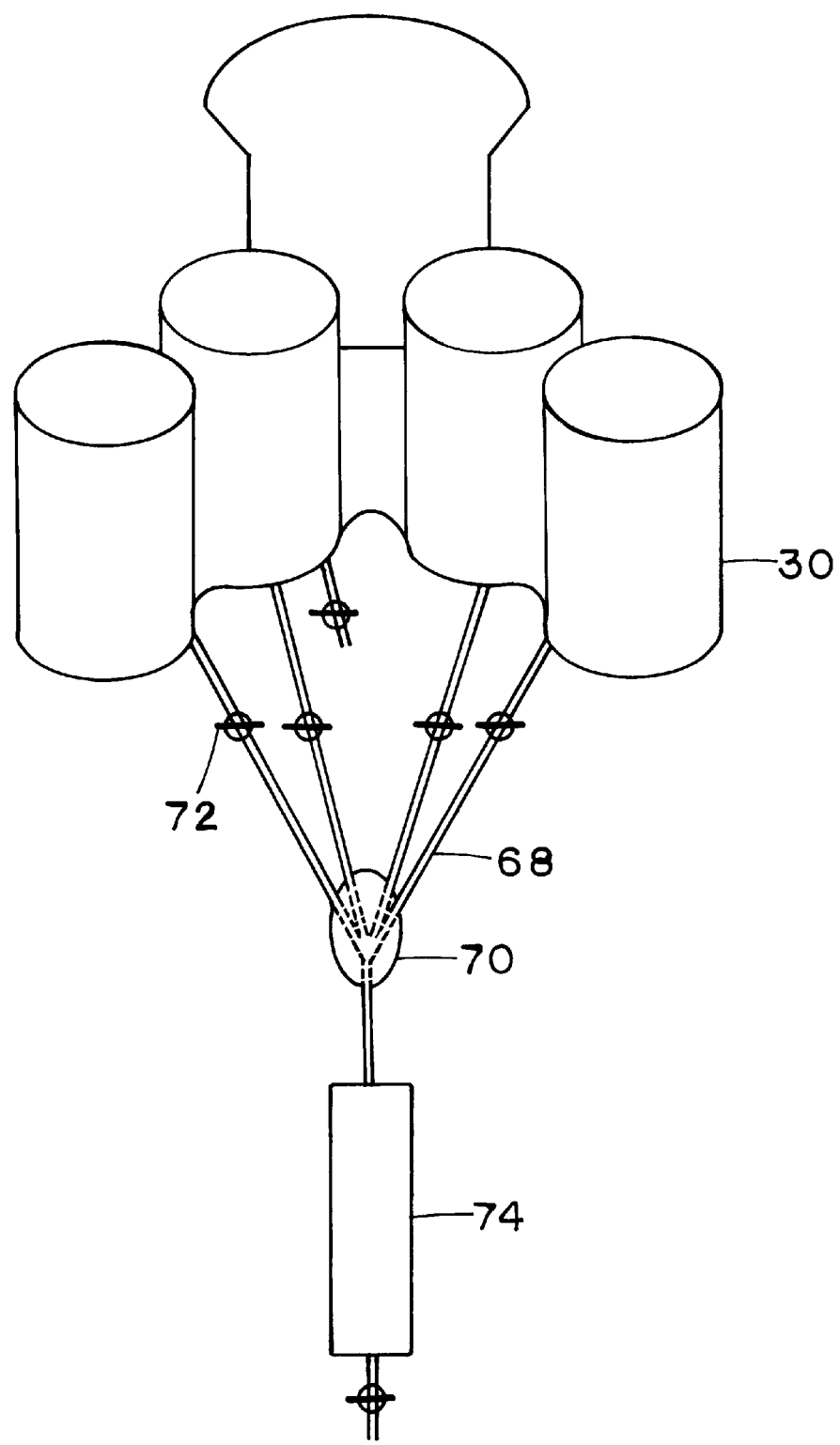
FIG. 12 shows location of buffer distributor.

Buffer distributor 70 is an oval disc made of acrylic having length between 1.5" to 2", width between 1" to 1.5" and thickness between 0.3" to 0.5" (FIG. 11). From the lower end, approximately a 1" long vertical hole is drilled in the middle of its rim. From the top side, 4 separate holes are drilled at different angles making sure that they connect the hole from lower end in the middle of the disc (FIG. 12). In these holes, the distributor carries connecting tubes 71 (M, N, O, P, Q). These tubes, made of brass, are permanently fixed by using epoxy based adhesive. The size, shape and thickness of buffer distributor and connecting tubes can be varied as required.

Figure 10:
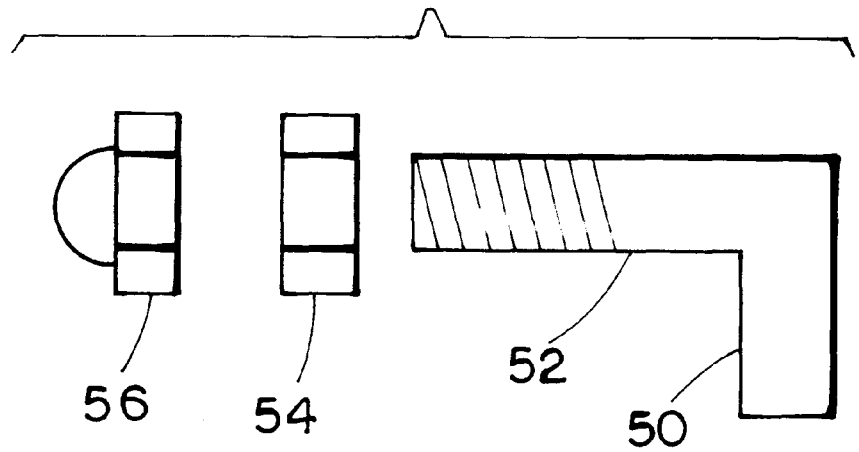
FIG. 10 shows details of hook.

The hook 38 is an "L" shaped metal rod, ranges in length between 1.5" to 2.5", and diameter between 0.3" to 0.5" (FIGS. 2, 10). It has a short arm 50 and a long arm 52, both exist at right angles to one another. The long arm has screw threads (16/inch) cut on its surface with a die to accept nuts. A hex nut 54 is threaded first and then, the long arm is passed through the hole 36 in the handle (FIG. 3). A cap nut 56 is then threaded. Both nuts are tightened across the handle top 34 making sure that short arm stays in the back of handle with its free end facing down (FIG. 2).

Figure 9:
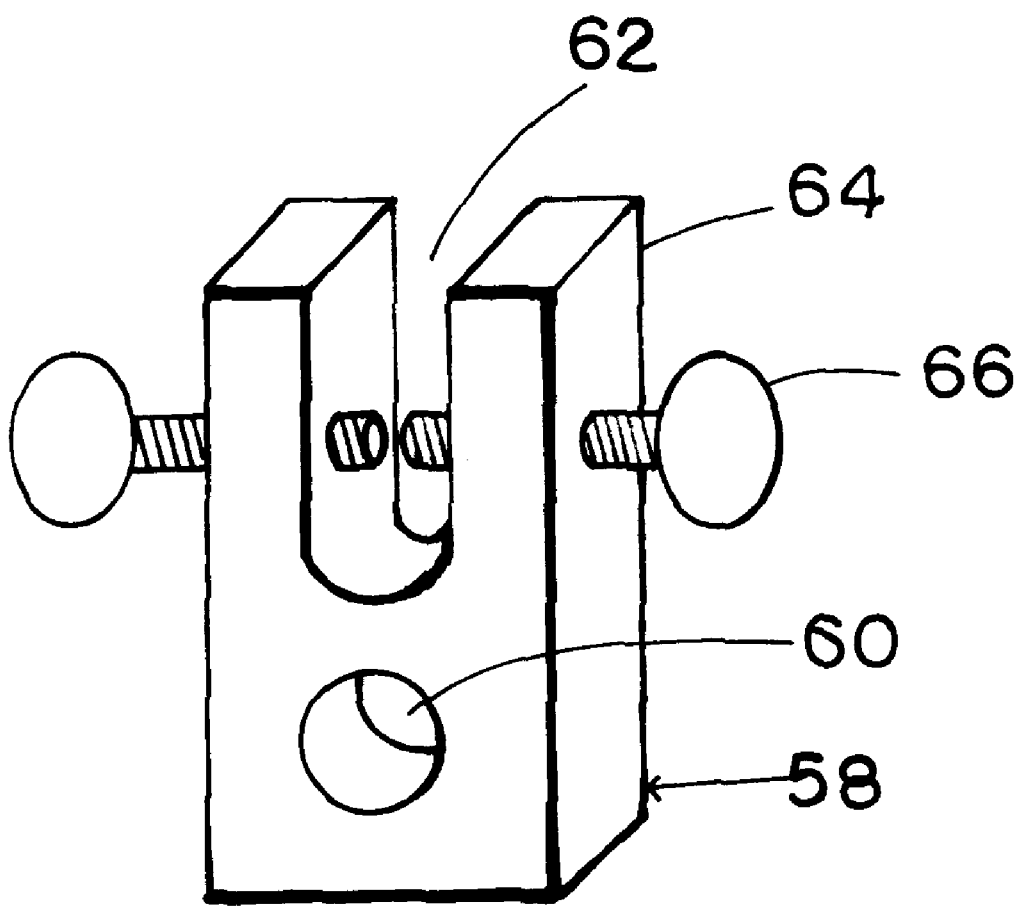
FIG. 9 shows clamp for holding the unit on a stand.

A clamp 58 (FIG. 9) is developed to hold Chromatography Buffers Center on a stand. The clamp is fabricated from a piece of metal having a size ranging in length between 2" and 2.5", width between 1" and 1.5" and thickness between 0.5" and 1". Near one end, a hole 60 ranging in diameter between 0.3" to 0.5" is cut across the plate. From the other end of this square rod, a groove 62 ranging in width between 0.3" to 0.5" and length between 1" to 1.5" is cut to accept a vertical rod of common laboratory stand. A narrow hole having a diameter approximately 0.25" is drilled in the middle of each side 64 of the groove. Using a suitable tap, screw thread (16/inch) is cut in both narrow holes to accept a 1" long thumb screw 66. These thumb screws when tightened hold the clamp tightly to the rod of laboratory stand. The hole 60 of clamp accepts hook 38 that is attached to handle top 34.

Operation

Described below is a procedure for adding 4 different types of buffers to chromatography column by gravity.

1. Place hook 38 of the unit in hole 60 of clamp 58 attached to the rod of a common laboratory stand. The unit can also be made to sit on a flat surface.
2. Attach a flexible plastic tubing 68 of required length to a drain tube (for instance 28A, FIG. 1) on one end and to connecting tube (for instance 71P) of buffer distributor 70 on the other (FIG. 11).
3. Introduce a stop-cock 72 in the middle of tubing.
4. Add required volume of buffer to reservoir of drain tube 28A, Open the stop-cock to let buffer flow into the tubing. Close the stop-cock when buffer comes out of connecting tube 71Q of buffer distributor 70 (FIG. 11).
5. Repeat this procedure for other reservoirs.
6. Prior to adding buffer to second reservoir, close one of the two drain tubes (28B or 28C) by attaching a short tubing containing a stop-cock (FIG. 12). Close this stop-cock.
7. Connect tube 71Q of buffer distributor 70 to the top of column 74 by a tubing. Cover each reservoir with lid 42.
8. To develop column, open stop-cock so that required volume of desired buffer passes through. Open the stop-cock of column outlet.
9. Complete chromatography by passing various buffers in a sequence as required by experimental protocol. Collect eluate from the column for analysis of desired molecules.

During the run more buffer can be added to any reservoir by removing lid. At the end of chromatography, residual buffers can be stored in the same unit for the next run. When not in use, to drain buffer or washings, support lids in place and tilt the unit in a sink by holding handle. Lids drain liquid through their deep grooves in seconds. Finally, rinse and air dry the apparatus for next use.

Apply the following additional steps to prepare a buffer containing salt gradient, for instance. Introduce these modifications where needed in the previous procedure.

Figure 13:
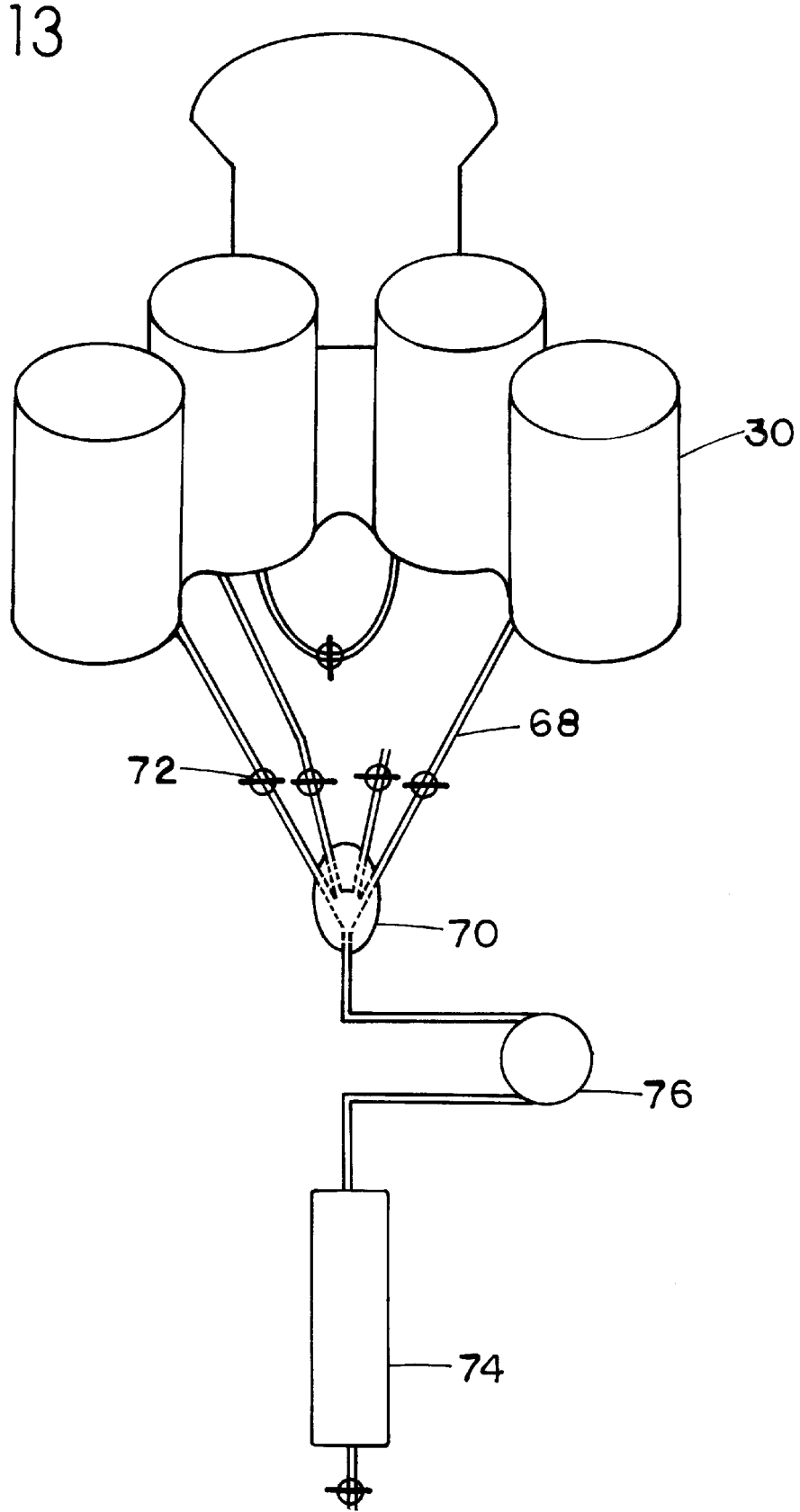
FIG. 13 shows location of peristaltic pump.

10. Connect a tubing to drain tube 28C on one end and to 28D on the other. Introduce a stop-cock in the middle of the tubing (FIG. 13).
11. Add buffer containing high concentration of salt to reservoir of drain tube 28D.
12. Open stop-cock so that high salt buffer flows by expelling air present in the tubing. Stop the flow when buffer reaches the reservoir of drain tube 28C.
13. Close one of the connecting tubes 71N of buffer distributor by attaching a short tubing having a stop-cock (FIG. 13). Close this stop-cock.
14. Place a suitable spin bar in reservoir of drain tube 28C.
15. Attach a suitably long flexible plastic tubing to drain tube 28B on one end and to buffer distributor on the other. Introduce stop-cock in the middle (FIG. 13).
16. Add required volume of low salt buffer to reservoir of drain tube 28B.
17. Prior to starting the gradient, adjust the horizontal position of Chromatography Buffers Center with a level.
18. By using a magnetic stirrer, spin bar magnet to mix low salt buffer.
19. Open stop-cock so that high salt and low salt buffers mix gradually, form a gradient and flow into the column.

At the end of gradient, pass various other buffers as required through column to complete the run.

The above described procedures can also be completed by using a peristaltic pump 76 between buffer distributor and the chromatography column (FIG. 13). By manually opening and closing the stop-cocks to let required buffers flow, different proteins can be successfully isolated.

Figure 14:
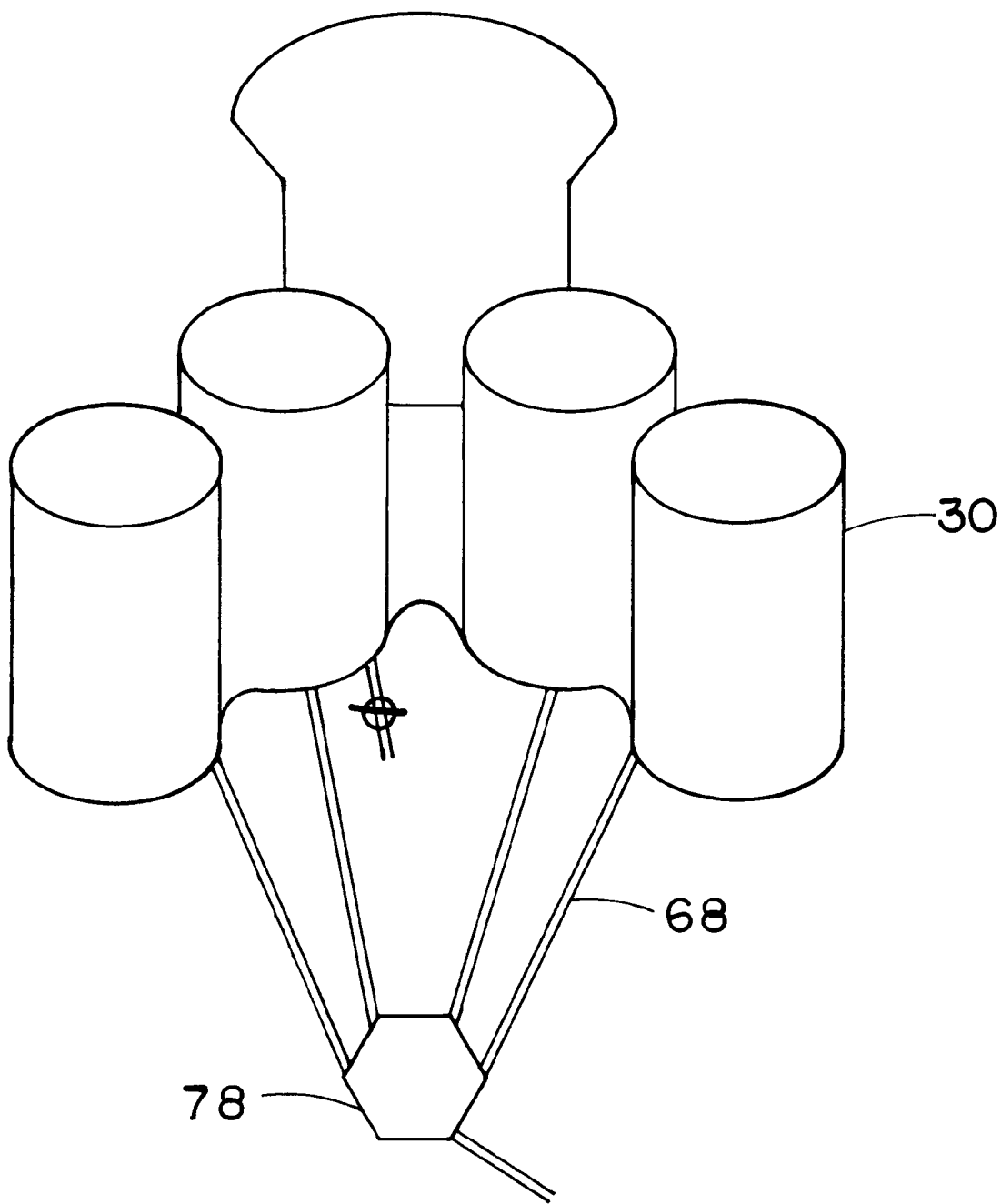
FIG. 14 shows location of valve regulator.

Buffer distributor can be totally eliminated by connecting Chromatography Buffers Center to instruments having valve regulator 78 (FIG. 14). After adding buffers to reservoirs, stop-cocks can be fully open leaving the control of buffer flow totally to the instrument. Stop-cocks can also be totally eliminated (FIG. 14).

Therefore, Chromatography Buffers Center can be used to develop columns by using gravity, peristaltic pump or instruments having valve regulator. Besides, the unit with 4 reservoirs can also be used for only 3 types of buffers by letting one reservoir go empty. Alternately, two reservoirs can be made to supply one type of buffer. The apparatus can also be used only as a gradient maker. Therefore, this unit has many uses for performing a variety of experiments.

Description of Other Preferred Embodiments

The second preferred embodiment of the Chromatography Buffers Center contains five reservoirs with five lids. This unit is useful where five types of buffers are needed in a procedure. Its operation is similar to that of first preferred embodiment.

Figure 4:
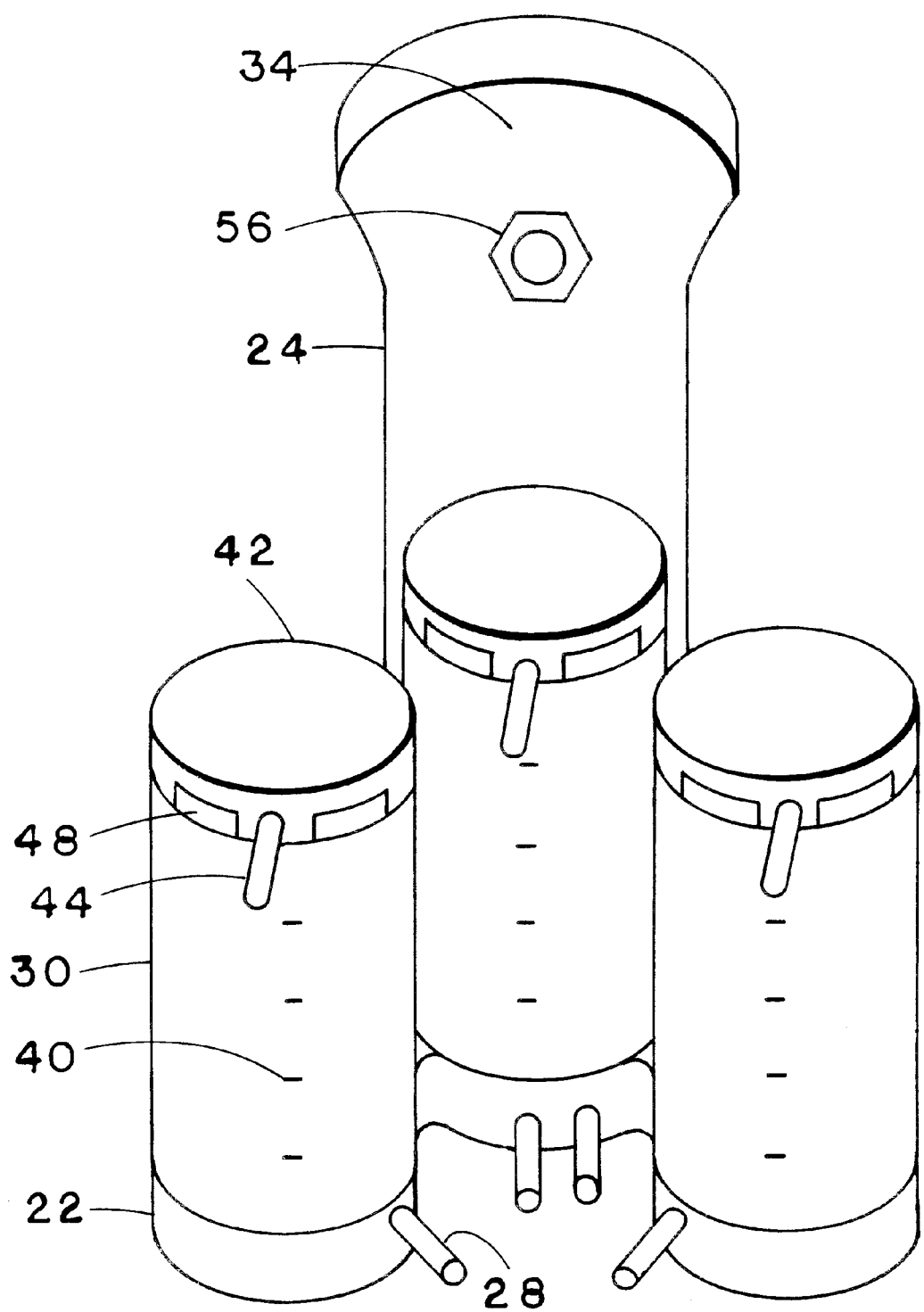
FIG. 4 shows a unit with three reservoirs.

The third preferred embodiment contains three reservoirs and three lids (FIG. 4). Its operation is similar to that of first preferred embodiment.

Figure 5:
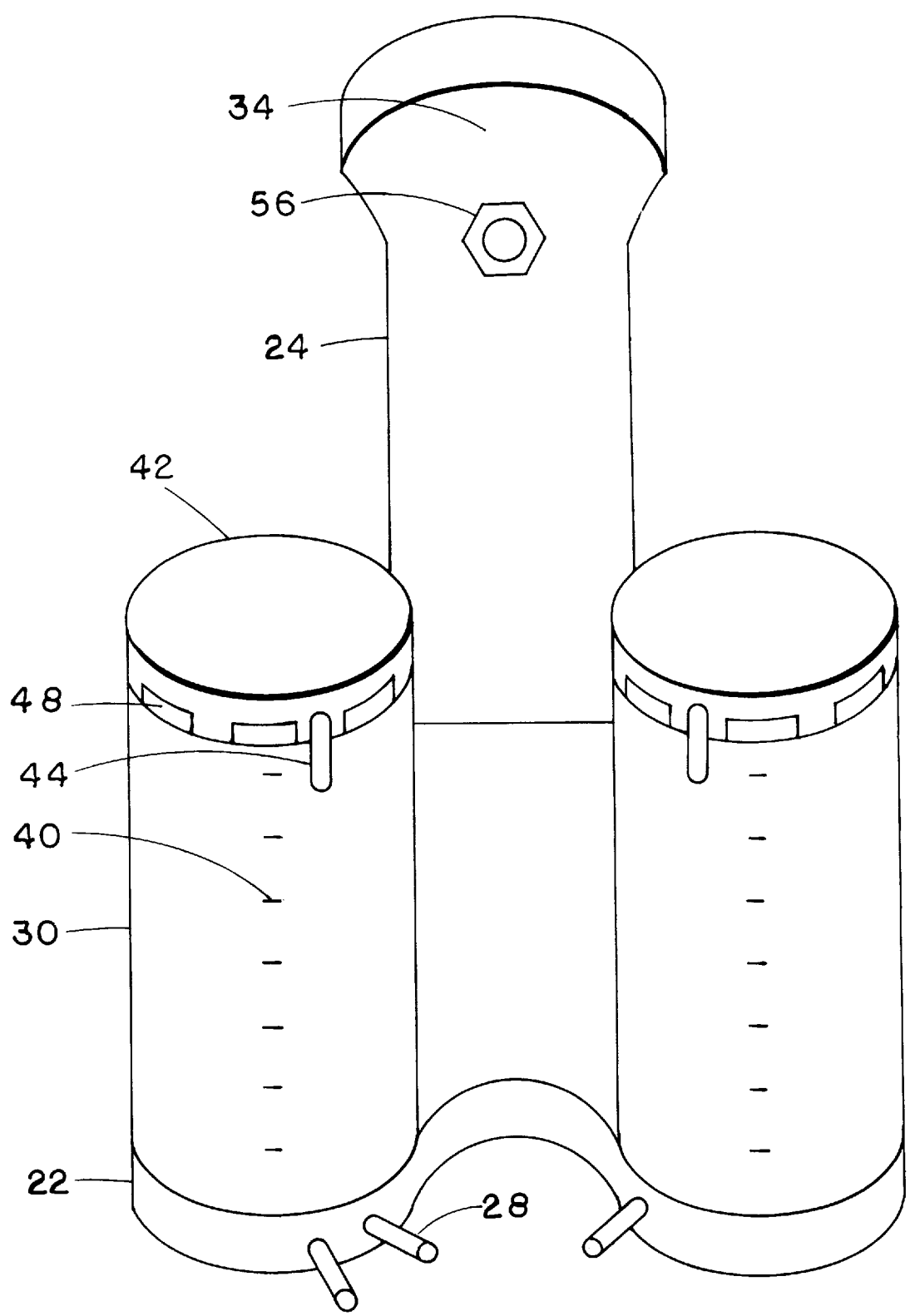
FIG. 5 shows a unit with two reservoirs.

The fourth preferred embodiment contains two buffer reservoirs with two lids (FIG. 5). It can also be used as a gradient maker.

Figure 6:
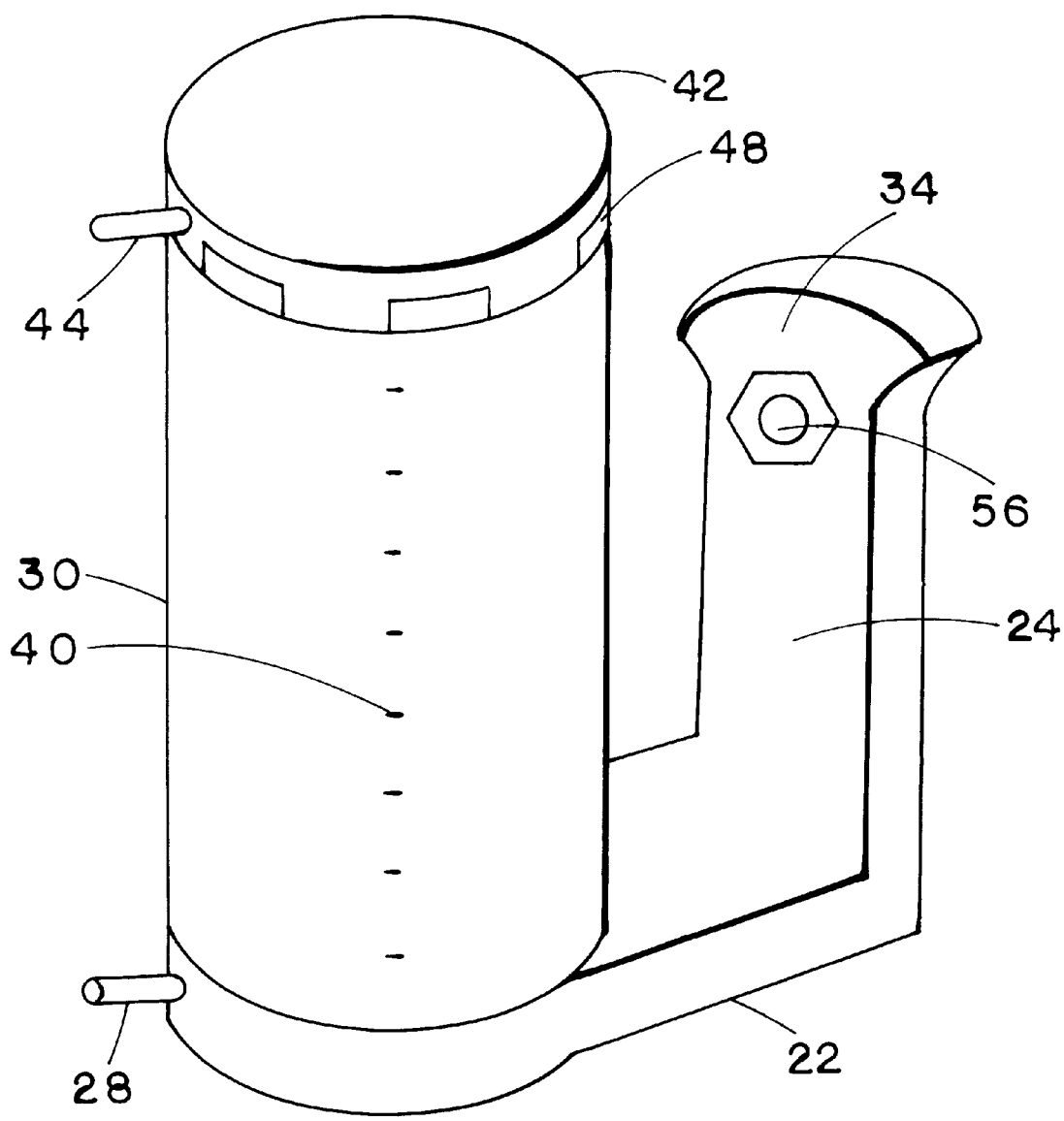
FIG. 6 shows a unit with one reservoir.

The fifth preferred embodiment has one reservoir with one lid (FIG. 6). One or more of these units can be used to separately hold buffers in different chromatography procedures. This type of embodiment is particularly useful for sieving column chromatography where one kind of buffer is needed in large volume.

Summary, Ramifications and Scope

From the above described information, the reader can see that various forms of Chromatography Buffers Center can be used in the purification of biological molecules by molecular sieving, ion-exchange, affinity and other types of chromatography procedures. The apparatus has several useful features. It can be carried with a proper grip. Buffers can be drawn from the bottom of reservoirs. More fresh buffer can be added to reservoir easily at any time. Lid protects buffer from surface evaporation and air born dust. The unit needs little or no maintenance. It is simple to use.

Eventhough the basic details of the invention and different embodiments are shown in various figures, it is understood that additional changes in size, shape, structure and materials can be made without greatly departing from the original conception. For instance, some reservoirs can be made larger than others. Some possible other modifications of the invention are described below.

Base plate contains a separate piece of either metal or plastic attached as handle. Disadvantage is that it is not very sturdy when compared to a handle derived by extending and bending the same base plate. Also, attaching a separate piece needs additional work and materials.

Base plate contains no handle. Disadvantage is that unit can not be carried easily. Also, it can not be mounted on a column.

Providing Chromatography Buffers Center with a lid common to all reservoirs.

Individual lids are modified and attached to reservoirs with a hinge.

Replacing drain tube with a stop-cock in the base plate. However, stop-cocks are cumbersome to operate when present close to base plate and reservoir.

Mounting and removing the unit from clamp attached to a common laboratory stand is easy. There is no need for tightening and loosening nuts and bolts. Since buffer is drawn from the bottom of each reservoir by a permanently fixed drain tube, pumping air because of tubing end surfacing in buffer is totally eliminated. Also, buffer getting contaminated due to transfer of tubing from one reservoir to another is prevented. For positional adjustments, the hook in the hole of clamp moves side to side easily when the unit is pushed even by a finger.

The Chromatography Buffers Center can be used independently to feed columns with buffers by gravity. The flow of each buffer is regulated by a stop-cock. Hydrostatic pressure in each reservoir, automatically expels air present in the tubing. This eliminates the need for siphoning buffer by a syringe. The unit can also be used with peristaltic pump 76 and also with other instruments having valves 78 controlled by a computer. Therefore, this unit has multiple uses.

Lid of each reservoir is provided with special grooves not only to provide ventilation but also to drain buffer quickly and completely with lid sitting in its place. Winding tubing around reservoir first and then attaching to stop pin keeps it out of way for storing the unit. This is particularly convenient for the subsequent run because tubings need not be reassembled. Similarly, one can also save time that is generally spent looking for reservoirs of similar kind for holding buffers to perform any experiment. Transparency allows one to see the level of buffer in each reservoir. The unit costs less and easy to control.

From the above described summary, ramifications, scope and discussion it can be seen that one can mix and match several features and fabricate other types of Chromatography Buffers Centers. Therefore, the scope of the Chromatography Buffers Center should be determined not by the typical embodiment illustrated but by the appended claims and their legal equivalents.

I claim the following:

1. A Chromatography Buffers Center for holding different types of buffers, comprising:
   (a) a base plate of sufficient size for accommodating reservoirs,
   (b) a plurality of reservoirs for holding required volume of buffers,
   (c) a plurality of lids suitably modified for reservoirs,
   (d) a handle of suitable proportions with a hook attached,
   (e) a plurality of drain tubes in the base plate,
   (f) a clamp with a hole for the hook of handle and with a groove to receive the rod of a common laboratory stand, and
   (g) a buffer distributor with a plurality of connecting tubes so that various buffers present in the apparatus can be delivered to a column for isolating biological molecules by chromatography experiments in a scientific laboratory.

2. The Chromatography Buffers Center of claim 1, wherein said base plate, handle, reservoirs, lids and buffer distributor are made of acrylic.

3. The Chromatography Buffers Center of claim 1, wherein said base plate has plurality of drain tubes made cryptic in its rim.

4. The base plate of claim 3, wherein holes in the top of base plate communicating with drain tubes in the rim are encircled by reservoirs.

5. The Chromatography Buffers Center of claim 1, wherein said reservoirs having graduation marks are attached with one end to the top surface of said base plate so as to hold buffer.

6. The Chromatography Buffers Center of claim 1, wherein said handle, an extension of base plate, is separated along its length from reservoirs by a gap sufficient for a grip by human hand.

7. The Chromatography Buffers Center of claim 6, wherein said handle has a hole in the middle of its broad top to accept a hook.

8. The Chromatography Buffers Center of claim 1, wherein said lid has a groove of sufficient height and depth that runs at the lower edge in a circumferential manner so as to accommodate the rim of reservoir.

9. The Chromatography Buffers Center of claim 1, wherein said lid has a plurality of short deep grooves distributed evenly in the rim, communicate with the chamber of reservoir on one side and with the exterior on the other, thereby providing ventilation, and draining passages for liquid.

10. The Chromatography Buffers Center of claim 1 wherein, said lid has stop pin permanently fixed in the rim which instantly prevents the flow of buffer when a buffer draining tubing from a reservoir is attached.

11. The Chromatography Buffers Center of claim 1 wherein the clamp has predetermined dimensions, comprising:

(a) a hole of suitable diameter to receive short arm of hook present in the handle of scientific apparatus, (b) a groove of sufficient width and depth to receive a vertical rod of a common laboratory stand, and (c) thumb screws to hold clamp on the vertical rod, so that Chromatography Buffers Center can be mounted safely for doing experiments with columns.

12. The Chromatography Buffers Center clamp of claim 11 wherein said clamp is made of a metal that is light and hard.

13. The Chromatography Buffers Center of claim 11 wherein, the hole and groove cut both the top and bottom surfaces of the clamp.

14. The Chromatography Buffers Center of claim 11, wherein the thumb screws which upon tightening grip the rod of stand firmly at any given height.

15. The Chromatography Buffers Center hook of claim 1 wherein the hook has predetermined dimensions, comprising:

(a) a rod of suitable length bent to give a short arm and a long arm at rightangle to one another, and (b) the long arm having screw thread to accept a hex nut and a cap nut, so that long arm when passes through the hole present in the top of handle, holds the unit firmly between the hex nut and cap nut.

16. The Chromatography Buffers Center of claim 15 wherein the hook is made of a metal that is light and hard.

17. The Chromatography Buffers Center of claim 15, wherein said hook along with Chromatography Buffers Center easily moves either to left or to right in the hole of clamp.

18. The Chromatography Buffers Center of claim 1, wherein the buffer distributor has sufficient size, comprising:

(a) a body of predetermined dimensions, (b) a plurality of holes in the rim communicating with one another approximately in the middle of the body of distributor, and (c) a plurality of connecting tubes permanently fixed in the holes of distributor, so that buffers from different reservoirs can be directed to flow to the chromatography column via a common connecting tube.

19. The Chromatography Buffers Center claim of 18, wherein said holes drilled at suitable angles remain separate on the rim but communicate with each other at a common point in the body of the distributor.

* * * * *